(12) United States Patent
Dupau et al.

(10) Patent No.: US 7,754,929 B2
(45) Date of Patent: Jul. 13, 2010

(54) 1,4-HYDROGENATION OF SORBOL WITH RU COMPLEXES

(75) Inventors: Philippe Dupau, Bellegarde (FR); Lucia Bonomo, Bellegarde (FR)

(73) Assignee: Innovaroma SA, Acacias/Geneva (CH)

( * ) Notice: Subject to any disclaimer, the term of this patent is extended or adjusted under 35 U.S.C. 154(b) by 0 days.

(21) Appl. No.: 12/594,413

(22) PCT Filed: Apr. 2, 2008

(86) PCT No.: PCT/IB2008/051222

§ 371 (c)(1),
(2), (4) Date: Oct. 2, 2009

(87) PCT Pub. No.: WO2008/120174

PCT Pub. Date: Oct. 9, 2008

(65) Prior Publication Data

US 2010/0113844 A1 May 6, 2010

(30) Foreign Application Priority Data

Apr. 3, 2007 (EP) .................................. 07105557

(51) Int. Cl.
*C07C 29/17* (2006.01)
(52) U.S. Cl. ..................................................... 568/903
(58) Field of Classification Search .................. 568/903
See application file for complete search history.

(56) References Cited

FOREIGN PATENT DOCUMENTS

EP     1 394 170 A1    3/2004

OTHER PUBLICATIONS

International Search Report, application No. PCT/IB2008/051222, mailed Jul. 28, 2008.

Bouachir et al., "Preparation and Stoichiometric and Catalytic Reactivity of Hydrido Organometallic Ruthenium Complexes. X-ray Crystal Structure of [RuH($\eta^5$—$C_8H_{11}$)$_2$]BF$_4$," Organometallics, vol. 10, pp. 455-462 (1991).

Drießen-Hülscher et al., "Selective two-phase-hydrogenation of sorbic acid with novel water soluble ruthenium complexes," Journal of Organometallic Chemistry, vol. 570, pp. 141-146 (1998).

Drießen-Hölscher, "Application of Cp*-Ruthenium(II) Catalysts in Stereoselective Hydrogenation of Sorbic Acid," Synthetic Method of Organometallic and Inorganic Chemistry, vol. 10, pp. 95-98 (2002).

Fagan, "Structure and Chemistry of the Complex Tetrakis($\eta^5$—pentamethylcyclopentadienyl)tetrakis($\mu_3$-chloro)-tetraruthenium(II): A Useful Precursor to (Pentamethylcyclopentadienyl)ruthenium(0), -(II), and -(IV) Complexes," Organometallics, vol. 9, pp. 1843-1852 (1990).

Steines et al., "Stereoselective catalytic hydrogenation of sorbic acid and sorbic alcohol with new Cp*Ru complexes," Chem. Commun., pp. 217-218 (2000).

Steines et al., "An Ionic Liquid as Catalyst Medium for Stereoselective Hydrogenations of Sorbic Acid with Ruthenium Complexes," J. Prakt. Chem., vol. 342, No. 4, pp. 348-354 (2000).

*Primary Examiner*—Elvis O Price
(74) *Attorney, Agent, or Firm*—Winston & Strawn LLP

(57) ABSTRACT

The present invention relates to the use of Ru complexes, having a pentamethyl-cyclopentadienyl and a cyclooctadine as ligands, together with some acidic additives for improving the selectivity in the 1,4-hydrogenation of sorbol into the corresponding Z-alkene as major product.

8 Claims, No Drawings

1,4-HYDROGENATION OF SORBOL WITH RU COMPLEXES

This application is a 371 filing of International Patent Application PCT/IB2008/051222 filed Apr. 2, 2008.

TECHNICAL FIELD

The present invention relates to the field of catalytic hydrogenation and, more particularly, to the use of specific Ru complexes with cyclopentadienyl derivatives, as one of the ligands, in 1,4-hydrogenation processes for the reduction of sorbol into the corresponding Z-alkene, as major product.

PRIOR ART

Selective 1,4-hydrogenation of conjugated dienes, in general, into their Z-alkene is a very interesting reaction in organic chemistry, since it renders accessible a number of compounds which are obtained in general with a poor selectivity.

One of the mandatory and characterizing elements of such processes is the catalyst or the catalytic system. The development of useful catalysts or catalytic systems for the 1,4-hydrogenation of sorbol into the corresponding Z-alkene is still an important, difficult and unpredictable task in chemistry. The chemical industry is always eager for higher selectivity, as well as to maintain a high conversion or yield.

From the prior art it is known that sorbic acid can be hydrogenated into the corresponding Z-alkene in the presence of [(Cp*)RuCO(phosphine)](anion) or [(Cp*)RuCO(sorbic acid)](anion) complexes, (Cp* representing a $C_5Me_5$ or pentamethyl-cyclopentadienyl ligand; see Driessen et al, in Chem. Commun., 2000, 217 or in J. Organomet. Chem, 1998, 141), however the yields (conversions×selectivity) are quite low.

Furthermore, in EP 1394170, it is reported the cisoid hydrogenation of sorbic acid and sorbol using as catalytic systems the complex [(Dienyl)Ru(acyclic diene)](anion) (in particular [(Cp*)Ru(sorbic acid)](anion) or [(Cp*)Ru(sorbol)](anion). In this document it is expressively reported that the use of cyclic diene, instead of acyclic diene, is highly detrimental to the overall yield. The only conditions displayed as providing good yields require nitromethane as solvent, the latter being relatively toxic and hazardous for industrial applications. Finally, Table 4 of said document shows that the addition of Lewis acids is highly detrimental to the yields.

Therefore, there is a need for processes using alternative catalytic systems systems possibly providing high selectivity and/or conversions.

DESCRIPTION OF THE INVENTION

In order to overcome the problems aforementioned, the present invention relates to processes for the catalytic reduction by 1,4-hydrogenation, using molecular $H_2$, of sorbol (I) into the corresponding Z-alkene (II) (i.e. Z-hex-3-en-ol) characterized in that said process is carried out in the presence of at least an acidic additive of the type specified further below, the catalyst or pre-catalyst being a ruthenium complex comprising as ligand a cyclopentadienyl derivative.

The invention's process is shown in Scheme 1:

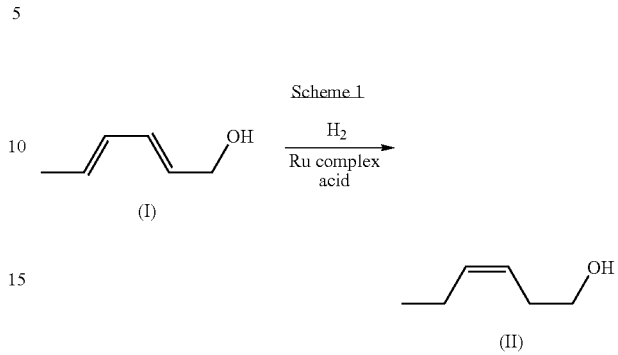

wherein compound (II) is in a Z configuration.

A particular embodiment of the invention is a process for the catalytic reduction by 1,4-hydrogenation, using molecular $H_2$, of sorbol of formula

into the corresponding Z-alkene, of formula

wherein the isomer of configuration Z is predominant;

said process being characterized in that it is carried out in the presence of at least one ruthenium catalyst or pre-catalyst of formula

$$[Ru(C_5Me_5)(COD)(L')_n]X \qquad (III)$$

wherein $C_5Me_5$ represents pentamethyl-cyclopentadienyl, COD a cyclooctadiene ligand and X represents a non coordinated anion, n represents 2, 1 or 0 and L' represents a solvent; and at least an acidic additive of the type described further below, preferably in a total amount of about 0.1, or even 0.2, to 100 molar equivalents, relative to the compound (III).

Concerning compound (II), since it is an olefin, it can be obtained in the form of a mixture of two isomers, i.e. the one having a configuration Z (Z-alkene (II)) or the one having a configuration E (E-alkene (II'))

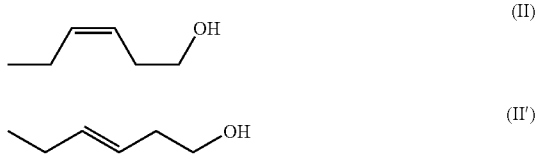

It is understood that according to the invention the alkene obtained is in the form of a mixture Z-alkene and E-alkene, wherein the ratio Z-alkene/E-alkene (Z/E) is above 1. According to a particular embodiment, said ratio is above 10 or even above 20. In another particular embodiment, said Z/E ratio can be above 30 or even above 35, and in some cases ratio of above 45 or more can be obtained. In any case the presence of the acidic additive in the prescribed concentration range allows to improve said ratio.

The substrate (I), due to the fact that it is a diene, can be in the form of a mixture of its three configuration isomers, i.e. the (Z,Z), (E,Z) and (E,E) isomers. According to a particular embodiment of the invention, said substrate can be essentially in the form of its (Z,Z) isomer (e.g. comprising at least 99% w/w of the isomer (Z,Z)).

The process of the invention is characterized by the use, as catalyst or pre-catalyst (hereinafter referred to as complexes unless specified otherwise), of a specific type of ruthenium complex as [Ru(C$_5$Me$_5$)(COD)(L')$_n$]X, as defined above.

According to a particular embodiment of the invention, L' can be acyclic or cyclic non aromatic ketones or esters, such as acetone or methyl acetate. The ketone can be coordinated in its enolic form.

The COD ligand can be any isomer of cyclooctadiene, namely cycloocta-1,5-diene (1,5-COD), cycloocta-1,4-diene (1,4-COD), cycloocta-1,3-diene (1,3-COD).

Particular examples of the non-coordinated anion X are ClO$_4^-$, R$^1$SO$_3^-$, wherein R$^1$ is a chlorine of fluoride atom or an C$_1$-C$_8$ fluoroalkyl or fluoroaryl group, BF$_4^-$, PF$_6^-$, SbCl$_6^-$, SbF$_6^-$, or BR$^2{}_4^-$, wherein R$^2$ is a phenyl group optionally substituted by one to five groups such as halide atoms or methyl or CF$_3$ groups.

According to a preferred embodiment of the invention, the anion is BF$_4^-$, PF$_6^-$, ClO$_4^-$, C$_6$F$_5$SO$_3^-$, BPh$_4^-$, CF$_3$SO$_3^-$ or yet B[3,5-(CF$_3$)$_2$C$_6$H$_4$]$_4^-$, even more preferably BF$_4^-$.

As examples of the complex (III) one may cite the following: [Ru(C$_5$Me$_5$)(1,3-COD)]BF$_4$.

In a general way, the complexes of formula (III) can be prepared and isolated prior to their use in the process according to the general methods described in the literature (for example see F. Bouachir et al.; *Organometallics*, 1991, pg 455).

It is also understood that the complex of formula (III) can also be obtained in situ from complexes which have a similar formula and are cationic or anionic according to the standard knowledge of a person skilled in the art. For example, reaction can be run using [Ru(C$_5$Me$_5$)(COD)Y] (Y being F, Cl, Br or I and method for preparation having been described by P. J. Fagan et al. in *Organometallics*, 1990, 9, pg 1843-1852) as precursors in the presence of the substrate and silver or tallium salts).

To carry out the processes of the invention it is required also to use at least an acidic additive. By "acidic additive" it is meant a compound capable of providing at least one proton to the catalytic cycle. Said acidic additive is preferably an organic or inorganic acid having a pK$_a$ comprised between 0.8 and 7, but in the case of phenols or boron derivatives said pK$_a$ can range up to 10.

Furthermore, said acidic additive and can be selected from the group consisting of:
- a compound of formula R$^3{}_{(3-x)}$MO(OH)$_x$, wherein R$^3$ is a R$^4$ or R$^4$O group wherein R$^4$ is a C$_1$-C$_{10}$ group, M is P or As and x is 1 or 2; and
- a boron derivative of formula R$^3$B(OH)$_2$, wherein R$^3$ is as defined above; and
- phenol or a phenol substituted by up to three C$_1$-C$_4$ alkyl, alkoxy or carboxylic groups, nitro groups or halogen atoms; and
- a C$_1$-C$_{12}$ mono-carboxylic non-amino acid; and
- a HOOCCH═CHCOOH di-acide, and the tetronic acid.

By "mono-carboxylic non-amino acid" it is meant here a mono-carboxylic acid which is not substituted by a primary, secondary or tertiary amino group or heteroaromatic nitrogen derivatives.

According to a particular embodiment, said R$^3{}_{(3-x)}$MO(OH)$_x$ acids can be a derivative wherein R$^3$ is a C$_1$-C$_8$ alkyl or alkoxyl group or a C$_1$-C$_8$ phenyl or phenoxyl group optionally substituted, M is P or As and x is 1 or 2.

Similarly said R$^3$B(OH)$_2$ acids can be those wherein R$^3$ is a C$_1$-C$_8$ alkyl or alkoxyl group or a C$_1$-C$_8$ phenyl or phenoxyl group optionally substituted.

According to another embodiment of the invention, said acid can be the phenol or a phenol substituted by one C$_1$-C$_4$ alkyl, alkoxy or carboxylic group, a nitro group or a halogen atom.

Furthermore, according to another particular embodiment of the invention, said acidic additive can be a mono-carboxylic acid of formula R$^5$COOH, wherein R$^5$ represents a C$_1$-C$_{12}$ hydrocarbon group or a C$_1$-C$_{12}$ halogenated or per-halogenated hydrocarbon group, optionally substituted by one alcohol group or one or two ether or ester groups. According to a further embodiment, said carboxylic acid is advantageously selected from the group consisting of:
- a carboxylic acid of formula R$^5$COOH, wherein R$^5$ represents
- a halogenated or per-halogenated C$_1$-C$_8$ hydrocarbon group;
- a R$^6$CH(OR$^6$) group, R$^6$ being a hydrogen atom or a C$_1$-C$_6$ hydrocarbon group;
- a C$_1$-C$_{12}$ hydrocarbon group, optionally substituted by one or two ether or ester groups, the optional substituent being by one two or three C$_1$-C$_4$ alkyl, alkoxy or carboxylic groups, or nitro groups or halogen atoms.

One can cite, as non-limiting examples, of said acidic additive the following: (BuO)$_2$PO(OH), ($^t$BuO)$_2$PO(OH), (PhO)$_2$PO(OH), (PhCH$_2$O)$_2$PO(OH), $^t$BuPO(OH)$_2$, Ph$_2$PO(OH), PhPO(OH)$_2$, PhAsO(OH)$_2$, (Me)$_2$AsO(OH), CF$_3$COOH, HCF$_2$COOH, maleic or fumaric acid, glycolic acid, pyruvic acid, sorbic, acetic or oleic acid, tetronic acid, C$_6$H$_{13}$B(OH)$_2$, PhB(OH)$_2$, p-OMe-benzoic, benzoic or p-(COOMe)-benzoic acid, phenol, 3,5-dimethoxy-phenol or 2-methoxy-phenol. Of course, other suitable acidic additives responding to the above description can be used.

According to another embodiment of the invention, said acidic additive can be selected from the group consisting of:
- a compound of formula R$^3{}_2$MO(OH) or R$^3$MO(OH)$_2$, wherein R$^3$ is a C$_1$-C$_6$ alkyl or alkoxyl group or a C$_1$-C$_8$ phenyl or phenoxyl and M is P or As; and maleic or glycolic acid and an halogenated or per-halogenated $C_1$-$C_7$ mono-carboxylic acid.

As previously mentioned the processes of the invention consist in the hydrogenation of a substrate using a ruthenium complex and an acidic additive. A typical process implies the mixture of the substrate with the ruthenium complex, at least one acidic additive and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 0.01 mol % to 5 mol %, the molar percentage being relative to the amount of substrate. Preferably, the complex concentration will be comprised between 0.03 mol % to 2 mol %. It goes without saying that the optimum concentration of complex will depend, as the person skilled in the art knows, on the nature of the latter, on the nature of the substrate, on the nature of the solvent and on the pressure of $H_2$ used during the process, as well as the desired time of reaction.

Useful quantities of acidic additive, added to the reaction mixture, may be comprised in a relatively large range. Apart from the one above cited, one can cite, as non-limiting examples, total amounts ranging between 0.5 to 50 molar equivalents, relative to the complex, preferably 0.8 to 20, and even more preferably between about 2 and about 10 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include non-aromatic solvents such as $C_1$-$C_{12}$ non aromatic ketones, esters, alkanes ethers, chlorinated alkanes and alcohols or mixtures thereof. According to an embodiment of the invention the solvent is advantageously selected amongst the $C_1$-$C_{12}$ alkyl ketones, esters, ethers or chlorinated alkanes and mixtures thereof. In particular and as non-limiting examples one may cite the following: acetone ethyl acetate, MTBE, THF, iso-propyl acetate, $Et_2O$, dichloromethane, 1,2-dichloethane, EtOH, MeOH, pentane, hexane. The choice of the solvent can be done as a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars) or even more if desired. Again, a person skilled in the art is well able to adjust the pressure as a function of the catalyst load and of the dilution of the substrate in the solvent. As examples, one can cite typical pressures of 1 to $30 \times 10^5$ Pa (1 to 30 bar).

The temperature at which the hydrogenation can be carried out is comprised between 0° C. and 120° C., more preferably in the range of between 40° C. and 100° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. $H_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz) spectrometer and normally measured at 300 K, in $CDCl_3$ unless indicated otherwise. Chemical shifts are listed in ppm.

Example 1

Hydrogenation Processes According to the Invention

Typical Hydrogenation Reaction Procedure 2,4-Haxanedienol, solvent, [Ru($C_5Me_5$)(COD)]X and the acidic additive according to the invention were loaded altogether under inert atmosphere an autoclave and the mixture was purged at room temperature with nitrogen (2 bars, 3 times) and then hydrogen (2 bars, 3 times) under stirring. The autoclave was then pressurized to the desired hydrogen pressure and heated at the desired temperature. The reaction was followed by hydrogen absorption monitoring and/or GC analysis sampling. The ruthenium catalyst was easily removed by distillation on residues and product isomers mixture was usually recovered in more than 90% molar yield.

The results obtained are summarized in the following tables.

TABLE 1 influence of the acidic additive and of its presence on hydrogenation selectivity reaction type:

2,4-hexadienol → [Ru($C_5Me_5$)(1,3-COD)]$BF_4$ (0.05 mol. %), acidic additive (0.25 mol. %), $H_2$ (5 bars), 70° C., acetone (50 wt. %)

complete conversion

| Acidic additive | 1,4-Selectivity | Ratio "cis"-alkene/"trans"-alkene |
| --- | --- | --- |
| none | >98% | 90/10 |
| Benzoic acid | >98% | 93/7 |
| ($C_6H_{13}$)B(OH)$_2$ | >98% | 93.5/6.5 |
| Acetic acid | >98% | 94/6 |
| Sorbic acid | >98% | 95/5 |
| Fumaric acid | >98% | 95.5/4.5 |
| Glycolic acid | >98% | 96/4 |
| (PhO)$_2$P(O)(OH) | >98% | 96.5/3.5 |
| (PhCH$_2$O)$_2$P(O)(OH) | >98% | 97/3 |
| (Ph)As(O)(OH)$_2$ | >98% | 97/3 |
| ((tBu)P(O)(OH)$_2$ | >98% | 97/3 |
| (Ph)P(O)(OH)$_2$ | >98% | 97.5/2.5 |
| trifluoroacetic acid | >98% | 97.5/2.5 |
| (Me)$_2$As(O)(OH) | >98% | 98/2 |
| (Ph)$_2$P(O)(OH) | >98% | 98/2 |
| ((BuO)$_2$P(O)(OH) | >98% | 98.5/1.5 |
| Maleic acid | >98% | 99/1 |
| cathecol | >98% | 94/6 |

TABLE 1-continued influence of the acidic additive and of its
presence on hydrogenation selectivity reaction type:

[Ru(C$_5$Me$_5$)(1,3-COD)]BF$_4$
(0.05 mol. %)
acidic additive (0.25 mol. %)
H$_2$ (5 bars),
70° C., acetone (50 wt. %)

2,4-hexadienol complete conversion

| Acidic additive | 1,4-Selectivity | Ratio "cis"-alkene/"trans"-alkene |
|---|---|---|
| p-cresol | >98% | 94/6 |
| pentafluorophenol | >98% | 94/6 |
| 2,4-dichloro-6-nitrophenol | >98% | 96/4 |
| 2-methoxyphenol | >98% | 97/3 |

TABLE 2 influence of the acidic additive and of its
presence on hydrogenation selectivity
influence of the anion X reaction type:

[Ru(C$_5$Me$_5$)(1,3-COD)]X
(0.05 mol. %)
(C$_6$H$_5$)$_2$P(O)(OH)
(none or 0.25 mol. %)
H$_2$ (5 bars),
70° C., acetone (50 wt. %)

2,4-hexadienol complete conversion

| X | Presence of diphenylphosphonic acid | 1,4-Selectivity | Ratio "cis"-alkene/"trans"-alkene |
|---|---|---|---|
| BF$_4^-$ | no | >98% | 90/10 |
| BF$_4^-$ | yes | >98% | 98/2 |
| ClO$_4^-$ | no | >98% | 82/18 |
| ClO$_4^-$ | yes | >98% | 97/3 |
| CF$_3$SO$_3^-$ | no | >98% | 90/10 |
| CF$_3$SO$_3^-$ | yes | >98% | 98/2 |
| PF$_6^-$ | no | >98% | 90/10 |
| PF$_6^-$ | yes | >98% | 98/2 |

The invention claimed is:

1. A process for the catalytic reduction by 1,4-hydrogenation, using molecular H$_2$, of sorbol of formula

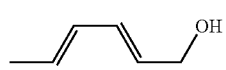

(I)

into the corresponding Z-alkene, of formula

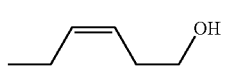

(II)

wherein the isomer of configuration Z is predominant;
wherein the process is carried out in the presence of
at least one ruthenium catalyst or pre-catalyst of formula $$[Ru(C_5Me_5)(COD)(L')_n]X \quad (III)$$

wherein C$_5$Me$_5$ represents pentamethyl-cyclopentadienyl, COD a cyclooctadiene ligand and X represents a non coordinated anion, n represents 2, 1 or 0 and L' represents a solvent; and at least one acidic additive selected from the group consisting of:
a compound of formula R$^3_{(3-x)}$MO(OH)$_x$, wherein R$^3$ is a R$^4$ or R$^4$O group wherein R$^4$ is a C$_1$-C$_{10}$ group, M is P or As and x is 1 or 2;
a boron derivative of formula R$^3$B(OH)$_2$, wherein R$^3$ is as defined above; and
phenol or a phenol substituted by up to three C$_1$-C$_4$ alkyl, alkoxy or carboxylic groups, nitro groups or halogen atoms;

C$_1$-C$_{12}$ mono-carboxylic non-amino acid;
a HOOCCH=CHCOOH di-acid, and the tetronic acid.

2. A process according to claim 1, wherein COD is cycloocta-1,5-diene, cycloocta-1,4-diene, cycloocta-1,3-diene.

3. A process according to claim 1, wherein X is ClO$_4^-$, R$^1$SO$_3^-$, wherein R$^1$ is a chlorine or fluorine atom or a C$_1$-C$_8$ fluoroalkyl or fluoroaryl group, BF$_4^-$, PF$_6^-$, SbCl$_6^-$, SbF$_6^-$, or BR$^2_4^-$, wherein R$^2$ is a phenyl group optionally substituted by one to five groups of halide atoms, methyl groups or CF$_3$ groups.

4. A process according to claim 1, wherein the at least one acidic additive is a mono-carboxylic acid is selected from the group consisting of:
a carboxylic acid of formula R$^5$COOH, wherein R$^5$ represents a halogenated or per-halogenated C$_1$-C$_8$ hydrocarbon group;
a R$^6$CH(OR$^6$) group, R$^6$ being a hydrogen atom or a C$_1$-C$_6$ hydrocarbon group; and
a C$_1$-C$_{12}$ hydrocarbon group, optionally substituted by one or two ether or ester groups, with the optional substituent being one, two or three C$_1$-C$_4$ alkyl, alkoxy or carboxylic groups, or nitro groups or halogen atoms.

5. A process according to claim 1, wherein the at least one acidic additive is selected from the group consisting of:
a compound of formula R$^3_2$MO(OH) or R$^3$MO(OH)$_2$, wherein R$^3$ is a C$_1$-C$_6$ alkyl or alkoxyl group or a C$_1$-C$_8$ phenyl or phenoxyl and M is P or As; and
maleic or glycolic acid and an halogenated or per-halogenated C$_1$-C$_7$ mono-carboxylic acid.

6. A process according to claim 1, wherein the at least one acidic additive is (BuO)$_2$PO(OH), ($^t$BuO)$_2$PO(OH), (PhO)$_2$PO(OH), (PhCH$_2$O)$_2$PO(OH), $^t$BuPO(OH)$_2$, Ph$_2$PO(OH), PhPO(OH)$_2$, PhAsO(OH)$_2$, (Me)$_2$AsO(OH), CF$_3$COOH, HCF$_2$COOH, maleic or fumaric acid, glycolic acid, pyruvic acid, sorbic, acetic or oleic acid, tetronic acid, C$_6$H$_{13}$B(OH)$_2$, PhB(OH)$_2$, p-OMe-benzoic, benzoic or p-(COOMe)-benzoic acid, phenol, 3,5-dimethoxy-phenol or 2-methoxy-phenol.

7. A process according to claim 1, wherein said process is carried out in the presence of a solvent selected amongst the C$_1$-C$_{12}$ alkyl ketones, esters, ethers or chlorinated alkanes and mixture thereof.

8. A process according to claim 1, wherein the at least one acidic additive is in a total amount of about 0.1 to 100 molar equivalents, relative to the compound (III).

* * * * *